United States Patent [19]

Kress et al.

[11] 4,252,955

[45] Feb. 24, 1981

[54] PROCESS FOR PREPARING 5-HALOPYRIMIDINES

[75] Inventors: Thomas J. Kress; Edward F. Szymanski, both of Indianapolis, Ind.

[73] Assignee: Eli Lilly and Company, Indianapolis, Ind.

[21] Appl. No.: 90,781

[22] Filed: Nov. 2, 1979

[51] Int. Cl.³ .......................................... C07D 239/30
[52] U.S. Cl. .................................................... 544/334
[58] Field of Search ................................ 544/334, 242

[56] References Cited

U.S. PATENT DOCUMENTS 3,824,292  7/1974  Kirby ................................... 260/602

OTHER PUBLICATIONS

Bredereck et al., Chem. Ber., 95 803–809 (1962).
Budesinsky, Coll. Czech. Chem. Comm. 14, 223–235 (1949).
McOmie et al., J. Chem. Soc. pp. 3129–3131 (1953).
Yanagita et al., J. Pharm. Soc. Japan 71, 39–40 (1951).
Yanagita, J. Pharm. Soc. Japan 72, 1383–1384 (1952).
Bredereck et al., Ber., 90 942–952 (1957).

Primary Examiner—Donald G. Daus
Assistant Examiner—M. C. Eakin
Attorney, Agent, or Firm—Joseph A. Jones; Arthur R. Whale

[57] ABSTRACT

The reaction of formamide at high temperature with a 4-halo-5-hydroxy-2(5H)-furanone provides high yields of 5-chloro or 5-bromopyrimidines.

16 Claims, No Drawings

PROCESS FOR PREPARING 5-HALOPYRIMIDINES

BACKGROUND

1. Field of the Invention

This invention provides an economical and convenient process for preparing 5-chloro- or 5-bromopyrimidine, by the high-temperature reaction of formamide with a 4-halo-5-hydroxy-2(5H)-furanone.

2. Prior Art

Pyrimidines have been studied by many organic chemists, and 5-halopyrimidines are frequently mentioned in the literature. For example, Kirby, U.S. Pat. No. 3,824,292, shows the preparation of 5-bromopyrimidine by the condensation of 2-bromo-3-methoxy-acrolein with formamide, citing Bredereck, Chem. Ber. 95, 803–09 (1962). The Bredereck article shows the preparation of 5-halopyrimidines by the reaction of formamide with 2-halotetraalkoxypropanes.

Another interesting preparation is shown by Budesinsky, Coll. Czech. Chem. Comm. 14, 223–35 (1949), C.A. 44, 1516e (1950), who prepared 4-carboxy-5-halo-2-substituted pyrimidines by the reaction of substituted amidines with 2,3-dihalo-3-carboxyacroleins.

A further item of interesting prior art is an article by Yanagita and Fukushima, J. Pharm. Soc. Japan 71, 39–40 (1951), who demonstrated the preparation of 5-chloro-2-aminopyrimidine by the reaction with guanidine of 2-chloro-3-hydroxyacrolein.

The invention described herein has a relationship to the processes of the prior art, but is clearly distinguished from the art by its ease and convenience, as well as by the obvious chemical distinctions.

SUMMARY OF THE INVENTION

This invention provides an economical and convenient process for preparing a 5-halopyrimidine of the formula

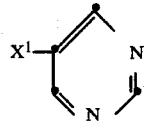

wherein $X^1$ is chloro or bromo, comprising contacting a 2(5H)-furanone of the formula

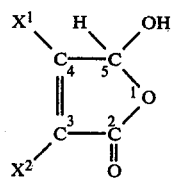

wherein $X^1$ is chloro or bromo, and $X^2$ is chloro, bromo, phenoxy, or phenoxy mono- or disubstituted with chloro, bromo, fluoro, $C_1$–$C_3$ alkyl, $C_1$–$C_3$ alkoxy, carboxy or amino which may be substituted with one or two $C_1$–$C_3$ alkyl groups, with at least about 5 moles of formamide per mole of 2(5H)-furanone at a temperature from about 150° to about 200°, and collecting the 5-halopyrimidine which distills from the reaction vessel.

DESCRIPTION OF THE PREFERRED EMBODIMENTS

Before the present invention is described in detail, some questions of nomenclature and terminology must be explained.

Temperatures are described in degrees Celsius throughout this document.

The terms $C_1$–$C_3$ alkyl and $C_1$–$C_3$ alkoxy include groups such as methyl, ethyl, propyl, methoxy, ethoxy, and isopropoxy.

The 2(5H)-furanones which are the starting compounds in this process have been called by various names in the past, which fact creates ambiguities in reading the art. These furanones have at times been named as derivatives of mucic acid, and so have been called mucochloric acid, mucobromic acid, mucophenoxychloric acid, mucobromochloric acid, and so forth. The compounds have also been called 3-formylacrylic acids, β-formylacrylic acids, 4-oxo-2-butenoic acids, and malealdehydic acids.

More importantly, the starting 2(5H)-furanones can exist in an open chain form, as follows:

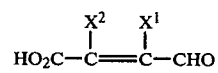

In the open chain form, the starting compounds could be named as 2-halo-3-carboxyacroleins. In the present document, however, the compounds will be considered as existing in the cyclic form, although it must be recognized by the reader that the starting compounds actually exist in equilibrium between the cyclic and open-chain forms.

Examination of the formulae of the products and starting compounds of this process shows that the 5-halo substituent of the product is the $X^1$ substituent of the starting compound. Thus, if 5-bromopyrimidine is desired, the $X^1$ substituent of the starting compound will be a bromine atom.

It will also be observed that every mole of product to be made requires one mole of the furanone and two moles of formamide. The physical requirements of the process, however, call for each mole of furanone to be contacted with at least about 5 moles of formamide. Larger amounts of formamide, in the range of from about 5 to about 15 moles per mole of furanone, may be used. The most advantageous ratio of the reactants is from about 8 to about 12 moles of formamide per mole of furanone.

The reaction is carried out at rather high temperatures, from about 150° to about 200°, and preferably from about 175° to about 185°. The high temperature of the reaction not only brings about a very prompt conversion to the desired product, but also enables the facile isolation of the product, which distills from the reaction mixture as it is formed.

It is preferred to carry out the reaction of this process in the presence of boric acid or boric anhydride ($B_2O_3$). The boron compound is not essential to the preparation of 5-halopyrimidines by this process, but its use improves the yields of the process. It is preferred to use about ½ mole of the boron compound per mole of the furanone starting compound. Amounts of the boron compound from about 0.05 mole to about 1 mole per mole of furanone are likewise effective, and may be used as desired.

The speed of the reaction is very high at the elevated temperatures which are used. Accordingly, it is most advantageous to combine the reactants slowly, so that the reaction takes place very rapidly and the product distills from the reaction vessel as rapidly as it is formed. Most advantageously, a portion of formamide and the boron compound, if used, are placed in a reaction vessel at the desired temperature, and the furanone, dissolved in additional formamide, is added slowly to the reaction vessel.

Although the use of high-boiling reaction solvents has been found to be disadvantageous, the use of low-boiling liquids in the reaction mixture can be helpful to assist in the distillation. The examples illustrate the use of water and methanol for this purpose. Other low-boiling alcohols can also be used, including especially $C_1$-$C_3$ alkanols.

When a low-boiling liquid is used in the reaction mixture, it is most advantageously mixed with the furanone-formamide solution which is to be slowly added to the reaction vessel. In this way, the low-boiling liquid is made available continuously to assist in sweeping product vapors out of the reaction vessel.

It is possible, of course, simply to combine the reactants, preferably in the presence of a boron compound as described above, and raise the temperature to the described range, collecting the product as it distills from the reaction vessel. When the process is carried out in this manner, the reaction will be complete in quite short periods of time in the range of from about 1 minute to about 60 minutes after the temperature reaches the desired range. It is more advantageous, however, to add one of the reactants to the hot reaction vessel in a controlled slow manner, so that the reaction takes place as quickly as possible.

The 5-halopyrimidine product is readily isolated from the contents of the receiving flask, most easily by extracting it with an alkane, especially heptane. The product is then crystallized from the heptane in good yield and purity, and additional product is extracted from the aqueous layer from the heptane extraction with a solvent such as chloroform. The examples below further illustrate the isolation.

Both the starting compounds and the products of the reaction have been used before in the organic chemical art. The product 5-bromopyrimidine was used as a starting compound by Taylor et al, U.S. Pat. No. 3,868,244, who made 5-pyrimidinemethanols by the reaction of appropriately substituted ketones with it.

The other product of this process, 5-chloropyrimidine, has not yet found an economically important use. Its preparation is taught by Chan and Miller, Aust. J. Chem. 20, 1595–1600 (1967), who used a 5-step process beginning with the reaction of tetramethoxypropane with guanidine to form 2-aminopyrimidine. As is shown later on in this document, 5-chloropyrimidine is easily reacted with alkylating agents such as alkyllithiums to prepare 4-alkyl-5-chlorodihydropyrimidines, which are biologically active.

Organic chemists are aware of the starting furanones. Both 3,4-dichloro-5-hydroxy-2(5H)-furanone and 3,4-dibromo-5-hydroxy-2(5H)-furanone can now be purchased as articles of commerce. They are prepared by the halogenation of furfural as described in U.S. Pat. No. 2,821,553 and Organic Syntheses, Vol. IV, p. 688, John Wiley and Sons, New York (1963). The 3-bromo-4-chloro compound, is prepared as described by Kuh and Shepard, J. Am. Chem. Soc. 75, 4597–99 (1953).

The authors added furfural and chlorine continuously to a mixture of aqueous bromine and hydrobromic acid at 75°, and obtained a 90% yield of the desired compound. It should be noted that some of the dichloro compound is also produced, and should be separated before the intermediate is used.

The 3-phenoxy-4-halo furanones are prepared as described in U.S. Pat. No. 3,954,853, which shows the compounds (called malealdehydic acids in that patent) being made by the reaction of the corresponding phenol with a 3,4-dihalo-5-hydroxy-2(5H)-furanone in the presence of a strong base.

A group of representative furanone starting compounds will be mentioned to assure that the reader will fully understand the scope of starting compounds which may be used.

3,4-dibromo-5-hydroxy-2(5H)-furanone
3,4-dichloro-5-hydroxy-2(5H)-furanone
4-bromo-3-chloro-5-hydroxy-2(5H)-furanone
4-chloro-5-hydroxy-3-phenoxy-2(5H)-furanone
4-bromo-3-(2,4-dichlorophenoxy)-5-hydroxy-2(5H)-furanone
3-(3-bromophenoxy)-4-chloro-5-hydroxy-2(5H)-furanone
4-chloro-3-(3,5-difluorophenoxy)-5-hydroxy-2(5H)-furanone
4-chloro-5-hydroxy-3-(4-methylphenoxy)-2(5H)-furanone
4-bromo-3-(2,6-diethylphenoxy)-5-hydroxy-2(5H)-furanone
4-chloro-5-hydroxy-3-(3-isopropyl-2-methylphenoxy)-2(5H)-furanone
4-bromo-3-(4-chloro-2-methylphenoxy)-5-hydroxy-2(5H)-furanone
4-chloro-3-(3-ethyl-5-methoxyphenoxy)-5-hydroxy-2(5H)-furanone
4-bromo-3-(4-carboxyphenoxy)-5-hydroxy-2(5H)-furanone
4-chloro-5-hydroxy-3-(3-isopropoxyphenoxy)-2(5H)-furanone
3-(3-aminophenoxy)-4-chloro-5-hydroxy-2(5H)-furanone
4-bromo-5-hydroxy-3-(4-dimethylaminophenoxy)-2(5H)-furanone
4-bromo-3-(5-ethyl-2-methylaminophenoxy)-5-hydroxy-2(5H)-furanone
4-bromo-3-(3-bromo-5-dipropylaminophenoxy)-5-hydroxy-2(5H)-furanone The process of this invention is further explained by the following preparative examples. The products of all of the examples were identified by nuclear magnetic resonance analysis, using a 60-megahertz instrument and dissolving the compound in $CDCl_3$ for analysis.

EXAMPLE 1

A one-liter 3-necked round-bottomed flask was equipped with a 500-ml. addition funnel, a mechanical stirrer and a distillation adaptor which was connected to an ice-alcohol-cooled one-liter 3-necked flask equipped with a water-cooled condenser. The pot was charged with 35 g. of boric anhydride and 160 ml. of formamide. The mixture was heated to 180°–185°, and then a solution of 258 g. of 3,4-dibromo-5-hydroxy-2(5H)-furanone in 240 ml. of formamide and 120 ml. of methanol was added dropwise over a period of 70 minutes. The temperature was held at 180°–185° during the addition, and the reaction mixture constantly stirred.

As soon as the addition was started, 5-bromopyrimidine began to distill over into the collecting flask, and continued to do so through the course of the process. When the addition was over, the reaction mixture was held at constant temperature for 15 minutes, and then 200 ml. of water was added over a 15 minute period. Not much additional product steam-distilled when the water was added.

The receiving flask was then taken off the apparatus, and 140 ml. of heptane was added to its contents. The mixture was warmed to 50° under reflux. When the solid had dissolved, the organic layer was removed, reheated to 50°, and cooled. After it was held at 25° for several hours, it was placed in the refrigerator overnight. The mixture was filtered, and the solids were vacuum dried to give 43.5 g. of light tan product, m.p. 70°–72°. The filtrate was evaporated to dryness to give 10.1 g. of additional product.

The aqueous layer from the receiver was extracted with 110 ml. and 70 ml. portions of chloroform, and the organic layers were washed with 20 ml. of water. The organic portions were then dried and the solvent was evaporated to give 23.5 g. and 1.8 g., respectively, of impure product, m.p. 65°–68°.

All of the above portions of product were analyzed by nmr methods as described above and found to be 5-bromopyrimidine, showing the following characteristic nmr signals: δ9.15 (s, 1H), 8.80(s, 2H)

EXAMPLE 2

Apparatus was set up as described in Example 1, and the pot charged with 17.5 g. of boric anhydride and 80 ml. of formamide. The temperature of the reaction mixture was raised to 180°–185°, and a mixture of 106 g. of 4-bromo-3-chloro-5-hydroxy-2(5H)-furanone in 120 ml. of formamide and 60 ml. of methanol was added dropwise over a period of 65 minutes. The reaction mixture was stirred 15 minutes more at 180°–185° after the addition was complete, the reaction mixture was cooled to 150°, and 100 ml. of water was added over a 15 minute period.

The receiving flask was stored for 16 hours in the refrigerator, and 90 ml. of heptane was then added to it. The mixture was refluxed at about 40° to dissolve most of the solid. The upper layer was decanted off and stored at 0° for several hours. It was then filtered, and the solids were dried to give 8.4 g. of 5-bromopyrimidine. The filtrate was evaporated to dryness to obtain 16.3 g. of additional product.

The aqueous layer from the receiving flask was diluted with 80 ml. of additional water, and extracted twice with 80 ml. portions of chloroform. The organic portions were combined and evaporated to dryness to give 13.8 g. of additional product. The total crude yield was 48.5% of the theoretical yield.

The crude 5-bromopyrimidine was dissolved in 250 ml. of hot water and was steam-distilled to obtain 200 ml. of total distillate. The aqueous layer in the receiving flask was extracted twice with 200 ml. portions of dichloromethane and the organic portions were evaporated to obtain 35.3 g. of pure 5-bromopyrimidine, equivalent to 44% of theory. The product was identical to the product of Example 1 by nmr analysis.

EXAMPLE 3

To the reaction vessel of an apparatus as described in Example 1 was added 7.5 g. of boric anhydride and 30 ml. of formamide. The mixture was heated to 180°–185°, and a solution of 64.5 g. of 3,4-dibromo-5-hydroxy-2(5H)-furanone in 40 ml. of formamide was added dropwise over a period of 40 minutes. The distillation of 5-bromopyrimidine from the reaction vessel started as soon as the first few ml. of the furanone solution was added. After the addition was complete, the temperature of the reaction vessel was lowered to 150°, and 50 ml. of water was added to steam-distill the last traces of product.

To the contents of the receiving flask were added 6 g. of sodium chloride and 60 ml. of heptane, and the mixture was heated to 80°. The lower aqueous phase was separated, and the organic phase was collected and slowly cooled, finally in an ice bath at 5°. The slurry was filtered and the solids were dried to obtain 9 g. of product in the form of white platelets. The filtrate was evaporated to dryness to obtain 0.8 g. of additional product.

The aqueous phase obtained above was extracted with 100 ml. of chloroform, and the organic layer was dried with magnesium sulfate and evaporated to dryness to obtain 2.2 g. of additional product in the form of an off-white powder. The total yield amounted to 30% of the theoretical yield of the process. The product was found to be identical to the product of Example 1 by nmr analysis.

EXAMPLE 4

The process of Example 3 was repeated, except that no boron compound was used. The yield of the process was 3.3 g. crystallized from the heptane, 1.1 g. from evaporation of the heptane, and 2.5 g. from extraction of the aqueous layer, a total of 6.9 g. or 17% of theoretical yield.

EXAMPLE 5

An apparatus was set up as described in Example 1, and the reaction vessel was charged with 17.3 g. of boric anhydride and 40 ml. of formamide. The mixture was heated to 180°–183°, and maintained at that temperature. To the hot reaction mixture was added a solution of 64.5 g. of 3,4-dibromo-5-hydroxy-2(5H)-furanone in 60 ml. of formamide over a period of 35 minutes, while the reaction mixture was stirred constantly. After the addition had been accomplished, the reaction mixture was stirred for 15 minutes at constant temperature, and to it was added 75 ml. of water over a period of 10 minutes. The temperature of the reaction mixture decreased to 125° during the water addition.

To the contents of the receiver was then added 60 ml. of hot heptane, and the heptane extract was first cooled to ambient temperature and then placed in the refrigerator for 1 hour. The heptane slurry was then filtered and the solids were dried under vacuum to give 8.3 g. of platelet-like product. The filtrate was evaporated to dryness to give 1.3 g. of additional product.

The aqueous layer obtained above was neutralized to pH 7 with sodium hydroxide solution, and was extracted twice with 35 ml. portions of chloroform. The combined organic layers were washed with 20 ml. of water and dried over magnesium sulfate, and the solvent was evaporated off under vacuum to give 5.3 g. of additional product. The combined portions of product 5-bromopyrimidine amounted to 38% of the theoretical yield. The product was identical to the product of Example 1 by nmr analysis.

EXAMPLE 6

A mixture of 0.83 g. of boric anhydride, 6.45 g. of 3,4-dibromo-5-hydroxy-2(5H)-furanone and 10 ml. of formamide was added to a reaction flask equipped with a condenser and thermometer. The temperature of the mixture was closely observed while the mixture was stirred, and it was found that an exothermic reaction occurred which took the temperature to 160° at the end of 45 minutes. The temperature then began to decline, and heat was applied to raise the temperature slowly to 180° at 70 minutes after the mixture had been prepared. The temperature was held constant for 50 minutes more, when the apparatus was cooled to the ambient temperature. It was found that the condenser contained a small amount of colorless solid, which was washed with chloroform and analyzed by nmr to determine that it was 0.3 g. of 5-bromopyrimidine.

EXAMPLE 7

A reaction and distillation apparatus was set up as described in Example 1, and the reaction pot was charged with 6.5 g. of boric anhydride and 45 ml. of formamide. The mixture was heated to 183°, and a solution of 40 g. of 4-bromo-3-chloro-5-hydroxy-2(5H)-furanone in 45 ml. of formamide was added dropwise with stirring over a period of 30 minutes. After about half of the addition had been made, the stopcock failed and approximately 10 ml. of the solution was inadvertently added rather rapidly, resulting in the loss of some vapor through the condenser. After the addition was complete, the mixture was stirred an additional 15 minutes at constant temperature, and 50 ml. of water was then added over 5 minutes.

The contents of the receiver were extracted with 60 ml. of hot heptane and the organic layer was cooled and held at 5° for 90 minutes. The slurry was then filtered, and the solids were dried to obtain 6.0 g. of colorless product. The filtrate was evaporated to dryness to give 2.5 g. of additional product.

The aqueous layer obtained above was neutralized to pH 8 with 50% sodium hydroxide solution, and then extracted with 50 and 25 ml. portions of chloroform. The combined chloroform extracts were washed with water, dried over magnesium sulfate, and evaporated to dryness to give 2.4 g. of product. The total yield of 5-bromopyrimidine amounted to 36% of the theoretical yield; the product was identical to the product of Example 1 by nmr analysis.

EXAMPLE 8

An apparatus was set up as described in the example above, and the reaction vessel was charged with 8.7 g. of boric anhydride and 40 ml. of formamide and heated to 160°-165°. The reaction mixture was stirred and the temperature was held constant while a solution of 64.5 g. of 3,4-dibromo-5-hydroxy-2(5H)-furanone and 60 ml. of formamide was added dropwise over 40 minutes. The mixture was then stirred for 15 minutes at constant temperature, and 60 ml. of water was added slowly.

A 60 ml. portion of hot heptane was added to the contents of the receiving flask, and the product was worked up as described in Example 7 to obtain 5.5 g. of 5-bromopyrimidine, identical to the product of Example 1 by nmr analysis, a yield of 14%.

EXAMPLE 9

An apparatus was set up as described in the examples above, and 8.7 g. of boric anhydride and 40 ml. of formamide were added to the reaction pot. The mixture was heated to 180°-185°, and a mixture of 64.5 g. of 3,4-dibromo-5-hydroxy-2(5H)-furanone, 60 ml. of formamide, and 13.5 ml. of water was added dropwise with stirring over a period of 47 minutes. The reaction mixture was then stirred at constant temperature for 15 minutes more, and 50 ml. of water was added over 10 minutes.

To the contents of the receiver were then added 85 ml. of hot heptane, and the organic layer was cooled and filtered and the filtrate was concentrated to dryness to obtain a total of 10.5 g. of product. The aqueous layer obtained from the receiver was extracted with 50 ml. of chloroform, and the organic layer was washed with water, dried and concentrated to dryness under vacuum to obtain 5.4 g. of product. The total yield was 40% of theoretical, and the product was identical to the product of Example 1 by nmr analysis.

EXAMPLE 10

The process of this example was run according to the process of Example 9, except that 30 ml. of methanol was added to the furanone solution, instead of the water used in Example 9. The contents of the receiving flask were worked up as described in Example 9 to obtain a total of 18.6 g. of product, equivalent to 47% of the theoretical yield. The product 5-bromopyrimidine was identical to the product of Example 1 by nmr analysis.

EXAMPLE 11

The apparatus was set up in the usual manner, and 8.7 g. of boric anhydride and 40 ml. of formamide were charged to the reaction flask and heated to 180°-185°. A 64.5 g. portion of 3,4-dibromo-5-hydroxy-2(5H)-furanone dissolved in 60 ml. of formamide was added at constant temperature with stirring over 30 minutes. The mixture was then stirred for 15 minutes more at constant temperature, and the receiving flask was changed. A 75 ml. portion of heptane was added to the reaction flask with stirring over 15 minutes to assist in distilling the remaining 5-bromopyrimidine. The heptane distillate was evaporated to dryness to give 2.1 g. of oily solid which was found by nmr analysis to consist in large part of 5-bromopyrimidine.

The mixture in the first receiving flask was partitioned between 50 ml. of water and 60 ml. of dichloromethane, and the pH of the aqueous portion was adjusted to 9 with sodium hydroxide solution. The aqueous layer was extracted again with 60 ml. of dichloromethane, and the combined organic portions were concentrated to dryness under vacuum to give 16.7 g. of dry 5-bromopyrimidine, identical to the product of Example 1 by nmr analysis.

EXAMPLE 12

An apparatus such as has been described above was assembled, and 1.2 g. of boric anhydride and 40 ml. of formamide were charged to the reaction flask and heated to 180°-185°. A solution of 9.52 g. of 4-bromo-5-hydroxy-3-phenoxy-2(5H)-furanone and 50 ml. of formamide was added over a period of 25 minutes with stirring at constant temperature. After the addition was complete, the reaction mixture was stirred for 15 minutes more at constant temperature. The material in the receiving flask was then diluted with water, and the pH of the mixture was adjusted to 11 with 5 N sodium hydroxide solution. The basic aqueous mixture was then extracted twice with 40 ml. portions of dichloromethane, and the organic layers were combined and evaporated under vacuum to obtain 1.51 g. of 5-bromopyrimidine, identical to the product of Example 1 by nmr analysis.

EXAMPLE 13

An apparatus such as has been described in the examples above was assembled, and 8.7 g. of boric anhydride and 40 ml. of formamide were charged to the reaction flask and heated to 180°–183°. A solution of 42.2 g. of 3,4-dichloro-5-hydroxy-2(5H)-furanone in 60 ml. of formamide was added dropwise with stirring at constant temperature over 35 minutes. The mixture was then stirred at constant temperature for 15 minutes more, and 50 ml. of water was added over 10 minutes.

The mixture in the receiving flask was then treated with 70 ml. of pentane and warmed. The layers were separated, and the pH of the aqueous layer was adjusted to 10, with cooling, with 50% sodium hydroxide solution, and the aqueous layer was then added back to the pentane layer. An additional 15 ml. of pentane was added, and the layers were separated once more. The organic layer was held for 16 hours at −20°, and was then filtered and the solids were dried to give 14.2 g. of product. The filtrate was evaporated to dryness to give 2.5 g. of additional product.

The aqueous layer obtained above was extracted with 50 ml. of pentane and the solvent was evaporated under vacuum to obtain 1.1 g. of product. The total yields of 5-chloropyrimidine amounted to 63% of the theoretical yield. The product's melting point was 36.5°–37.5°, and nmr analysis showed the following characteristic peaks: δ9.08 (s, 1H), 8.71(s, 2H).

The following preparation illustrates the use of 5-chloropyrimidine as an intermediate for the preparation of 4-alkyl-5-chlorodihydropyrimidines.

PREPARATION 1

A 28.5 g. portion of 5-chloropyrimidine was combined with 370 ml. of tetrahydrofuran and the mixture was cooled to −95°. The temperature was held constant while 150 ml. of 15.2% n-butyllithium solution in hexane was added over a period of 55 minutes. The reaction mixture was then stirred for 15 minutes more, and was allowed to warm to ambient temperature. A 150 ml. portion of water was added, and the layers were separated. The organic layer was concentrated to a syrup under vacuum, and the syrup was dissolved in 175 ml. of toluene. The toluene solution was washed with 200 ml. of water made acid to pH 1 with hydrochloric acid. The acid aqueous phase was neutralized with 50% sodium hydroxide solution, and the 2-phase neutral mixture was extracted 3 times with 100 ml. portions of chloroform.

The chloroform layers were combined, dried over magnesium sulfate, and evaporated under vacuum to obtain 41.9 g. of a pale amber oil. Analysis by nmr of the oil showed that it was 6-butyl-5-chloro-1,6-dihydropyrimidine. The nmr spectrum showed characteristic peaks as follows: δ8.72(s, 1H), 6.54(s, 1H), 10.63 (broad s, 2H), 4.56(t, 1H), 1.0–2.0 (broad m, 9H).

The above crude product was slurried in diethyl ether, affording the hydrochloride salt of the above compound as a crystalline solid, which was recrystallized from boiling toluene to provide fine white needles, m.p. 139°–141°.

The product of the above preparation was shown to be active as an algicide in a test in which the compound, in the hydrochloride salt form, was introduced in a concentration of 10 parts per million by weight to water in which algae of the genera Chlorella, Scenedesmus and Anacystis were growing. The test was carried out indoors under intense artificial light. The compound killed all of the Anacystis algae, and severely injured the Chlorella and Scenedesmus.

We claim:

1. A process for preparing a 5-halopyrimidine of the formula

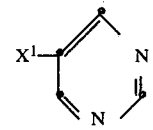

wherein $X^1$ is chloro or bromo, comprising contacting a 2(5H)-furanone of the formula

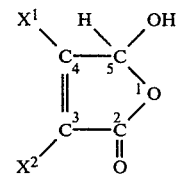

wherein $X^1$ is chloro or bromo, and $X^2$ is chloro, bromo, phenoxy, or phenoxy mono- or disubstituted with chloro, bromo, fluoro, $C_1$–$C_2$ alkyl, $C_1$–$C_3$ alkoxy, carboxy or amino which may be substituted with one or two $C_1$–$C_3$ alkyl groups, with at least about 5 moles of formamide per mole of 2(5H)-furanone at a temperature from about 150° to about 200°, and collecting the 5-halopyrimidine which distills from the reaction vessel.

2. A process of claim 1 wherein the contacting is in the presence of boric acid or boric anhydride.

3. A process of claim 1 wherein the temperature is from about 175° to about 185°.

4. A process of claim 1 wherein each mole of 2(5H)-furanone is contacted with from about 8 moles to about 12 moles of formamide.

5. A process of claim 1 wherein the 2(5H)-furanone is added slowly to the reaction mixture.

6. A process of claim 1 wherein the contacting is in the presence of water or a $C_1$–$C_3$ alkanol.

7. A process of claim 6 wherein the contacting is in the presence of methanol.

8. A process of claim 1, 2, 3, 4, 5, 6 or 7 for preparing 5-bromopyrimidine comprising contacting a 2(5H)-furanone wherein $X^1$ is bromo with formamide.

9. A process of claim 8 wherein the 2(5H)-furanone is 3,4-dibromo-5-hydroxy-2(5H)-furanone.

10. A process of claim 2 wherein the temperature is from about 175° to about 185°.

11. A process of claim 10 wherein the 2(5H)-furanone is added slowly to the reaction mixture.

12. A process of claim 11 wherein each mole of 2(5H)-furanone is contacted with from about 8 to about 12 moles of formamide.

13. A process of claim 12 wherein water or a $C_1$–$C_3$ alkanol is added slowly to the reaction mixture.

14. A process of claim 13 wherein methanol is added slowly to the reaction mixture.

15. A process of claim 10, 11, 12, 13 or 14 for preparing 5-bromopyrimidine comprising contacting a 2(5H)-furanone wherein $X^1$ is bromo with formamide.

16. A process of claim 15 wherein the 2(5H)-furanone is 3,4-dibromo-5-hydroxy-2(5H)-furanone.

* * * * *